(12) United States Patent
Matsunaga

(10) Patent No.: US 11,564,660 B2
(45) Date of Patent: Jan. 31, 2023

(54) ULTRASONIC DIAGNOSTIC APPARATUS AND METHOD FOR GENERATING ULTRASONIC IMAGE

(71) Applicant: Toshiba Medical Systems Corporation, Otawara (JP)

(72) Inventor: Satoshi Matsunaga, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 869 days.

(21) Appl. No.: 15/446,206

(22) Filed: Mar. 1, 2017

(65) Prior Publication Data

US 2017/0252010 A1    Sep. 7, 2017

(30) Foreign Application Priority Data

Mar. 4, 2016  (JP) .............................. JP2016-042614
Feb. 15, 2017  (JP) .............................. JP2017-025680

(51) Int. Cl.
*A61B 8/08* (2006.01)
*A61B 8/12* (2006.01)
*A61B 8/00* (2006.01)

(52) U.S. Cl.
CPC .............. *A61B 8/5207* (2013.01); *A61B 8/12* (2013.01); *A61B 8/4254* (2013.01);
(Continued)

(58) Field of Classification Search
CPC ......... A61B 8/12; A61B 8/4494; A61B 8/445; A61B 8/483; A61B 8/145; A61B 8/4483; A61B 8/463; A61B 8/4254; A61B 90/39
See application file for complete search history.

(56) References Cited

U.S. PATENT DOCUMENTS 5,295,486 A  *  3/1994  Wollschlager ......... A61B 5/352
                                                         600/447
5,876,345 A  *  3/1999  Eaton .................. G01S 15/8918
                                                         600/463

(Continued)

FOREIGN PATENT DOCUMENTS

JP         2-36854 A     2/1990
WO    WO 2013/021711 A   2/2013

OTHER PUBLICATIONS

Shung, "Diagnostic Ultrasound Imaging and Blood Flow Measurement", 2006 (Year: 2006).*

(Continued)

*Primary Examiner* — Colin T. Sakamoto
(74) *Attorney, Agent, or Firm* — Oblon, McClelland, Maier & Neustadt, L.L.P.

(57) ABSTRACT

An ultrasonic diagnostic apparatus according to the present embodiment includes an intracavitary ultrasonic probe, a memory circuit and a generation circuit. The probe includes first piezoelectric transducers performing ultrasonic transmission/reception along a first scan plane, and second piezoelectric transducers performing ultrasonic transmission/reception along a second scan plane. The memory circuit stores first information relating to a positional relationship between a sensor position and a position of the first scan plane, and second information relating to a positional relationship between a sensor position and a position of the second scan plane. The generation circuit generates first three-dimensional image data based on an output of the ultrasonic probe using the first piezoelectric transducers, an output of the sensor and the first information, and second three-dimensional image data based on an output of the ultrasonic probe using the second piezoelectric transducers, an output of the sensor, and the second information.

9 Claims, 10 Drawing Sheets

(52) U.S. Cl.
CPC ............ *A61B 8/4494* (2013.01); *A61B 8/466* (2013.01); *A61B 8/483* (2013.01)

(56) References Cited

U.S. PATENT DOCUMENTS

| | | | | |
|---|---|---|---|---|
| 6,045,508 | A * | 4/2000 | Hossack | G01S 15/8915 600/463 |
| 2005/0228275 | A1* | 10/2005 | Kawashima | A61B 8/12 600/437 |
| 2006/0034513 | A1* | 2/2006 | Cai | A61B 8/00 382/173 |
| 2006/0183992 | A1* | 8/2006 | Kawashima | A61B 8/12 600/478 |
| 2013/0338477 | A1* | 12/2013 | Glossop | A61B 10/0241 600/407 |
| 2017/0258446 | A1* | 9/2017 | Mao | G01S 15/899 |

OTHER PUBLICATIONS

Gee et al., "3D Ultrasound Probe Calibration Without a Position Sensor" University of Cambridge Sep. 2004 (Year: 2004).*

Ji et al., "Combining Multiple True 3D Ultrasound Image Volumes through Re-registration and Rasterization" Med Image Comput Comput Assist Interv. Oct. 1, 2009; 12(Pt. 1): 795-802 (Year: 2009).*

Japanese Office Action dated Nov. 17, 2020, issued in Japanese Patent Application No. 2017-025680.

* cited by examiner

ULTRASONIC DIAGNOSTIC APPARATUS AND METHOD FOR GENERATING ULTRASONIC IMAGE

CROSS-REFERENCE TO RELATED APPLICATION

This application is based upon and claims the benefit of priority from Japanese Patent Application No. 2016-42614, filed on Mar. 4, 2016, and Japanese Patent Application No. 2017-25680, filed on Feb. 15, 2017, the entire contents of each of which are incorporated herein by reference.

FIELD

An embodiment as an aspect of the present invention relates to an ultrasonic diagnostic apparatus and a method for generating an ultrasonic image.

BACKGROUND

In a medical field, an ultrasonic diagnostic apparatus which images an inside of an object by using ultrasonic waves generated by using piezoelectric transducers of an ultrasonic probe is in use. The ultrasonic diagnostic apparatus transmits the ultrasonic waves into the object from the ultrasonic probe connected to the ultrasonic diagnostic apparatus and allows the ultrasonic probe to receive a reflected wave caused by inconsistency of acoustic impedance inside the object. The ultrasonic diagnostic apparatus generates a received signal based on the reflected wave received by the ultrasonic probe and obtains a desired ultrasonic image by image processing.

A conventional art of the ultrasonic probe includes a multi-plane probe. An example of the multi-plane probe is a biplane probe including first piezoelectric transducers in which piezoelectric transducers are arranged on a plane orthogonal to an axis of a probe body and along an arc direction around an axis and second piezoelectric transducers in which piezoelectric transducers are arranged so as to be in parallel with the axis of the probe body.

An object of the present invention is to provide an ultrasonic diagnostic apparatus and a method for generating an ultrasonic image providing a three-dimensional image consistent with actuality in a case where a three-dimensional image is generated on each scan plane of the multi-plane probe.

BRIEF DESCRIPTION OF THE DRAWINGS

In accompanying drawings.

DETAILED DESCRIPTION

An ultrasonic diagnostic apparatus and a method for generating an ultrasonic image according to a present embodiment will be described with reference to attached drawings.

The ultrasonic diagnostic apparatus according to the present embodiment includes an intracavitary ultrasonic probe, a memory circuit and a generation circuit. The intracavitary ultrasonic probe includes first piezoelectric transducers performing ultrasonic transmission/reception along a first scan plane, and includes second piezoelectric transducers performing ultrasonic transmission/reception along a second scan plane different from the first scan plane. The memory circuit stores first information relating to a positional relationship between a position of a sensor attached on the ultrasonic probe and a position of the first scan plane, and stores second information relating to a positional relationship between a position of the sensor and a position of the second scan plane. The generation circuit generates first three-dimensional image data based on an output of the ultrasonic probe obtained by the ultrasonic transmission/reception using the first piezoelectric transducers, an output of the sensor and the first information, and generates second three-dimensional image data based on an output of the ultrasonic probe obtained by the ultrasonic transmission/reception using the second piezoelectric transducers, an output of the sensor, and the second information.

Figure 1:
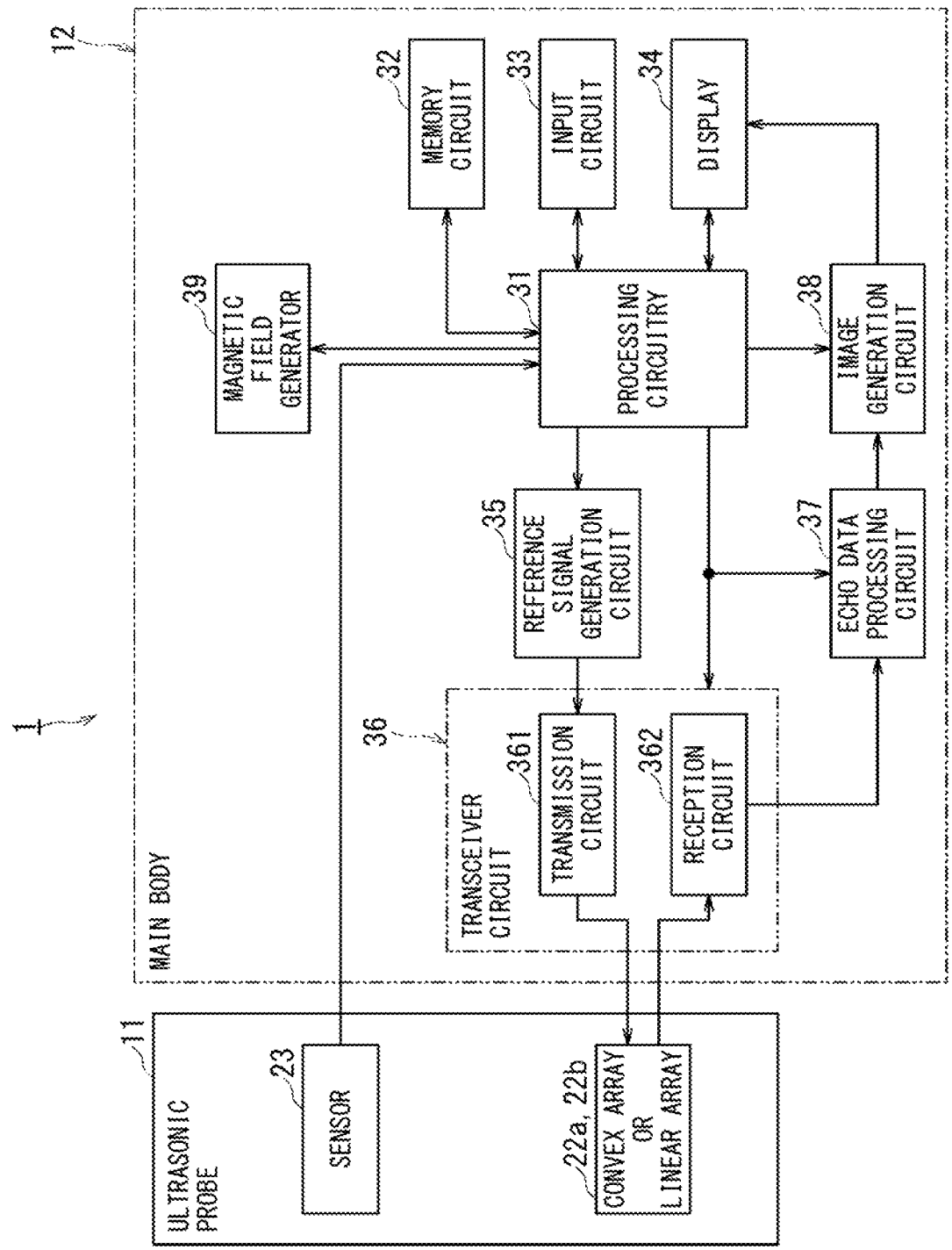
FIG. 1 is an outline diagram illustrating configuration of an ultrasonic diagnostic apparatus according to a present embodiment.

FIG. 1 is an outline diagram illustrating configuration of an ultrasonic diagnostic apparatus according to a present embodiment.

FIG. 1 illustrates the ultrasonic diagnostic apparatus 1 according to the present embodiment. The ultrasonic diagnostic apparatus 1 includes an ultrasonic probe 11 and a main body 12.

The ultrasonic probe 11 is an intracavitary multi-plane probe. The multi-plane probe includes a biplane probe capable of ultrasonic transmission/reception along each of two types of scan planes and a triplane probe capable of ultrasonic transmission/reception along each of three types of scan planes. A case where the ultrasonic probe 11 is a biplane probe will be described below. In the present embodiment, an intracavitary multi-plane probe suitable for imaging an internal organ by being inserted through a rectum will be described, but an external multi-plane probe may be used.

The ultrasonic probe 11 includes first piezoelectric transducers executing ultrasonic transmission/reception along a first scan plane (hereinafter referred to as a "first piezoelectric transducer set") and second piezoelectric transducers executing ultrasonic transmission/reception along a second scan plane different from the first scan plane (hereinafter referred to as a "second piezoelectric transducer set"). In the present embodiment, a case where the first scan plane and the second scan plane cross each other is described, but they may be in parallel with each other. In accordance with control by the main body 12, each of the first piezoelectric transducer set and the second piezoelectric transducer set transmits/receives ultrasonic waves to/from an object.

Figure 2:
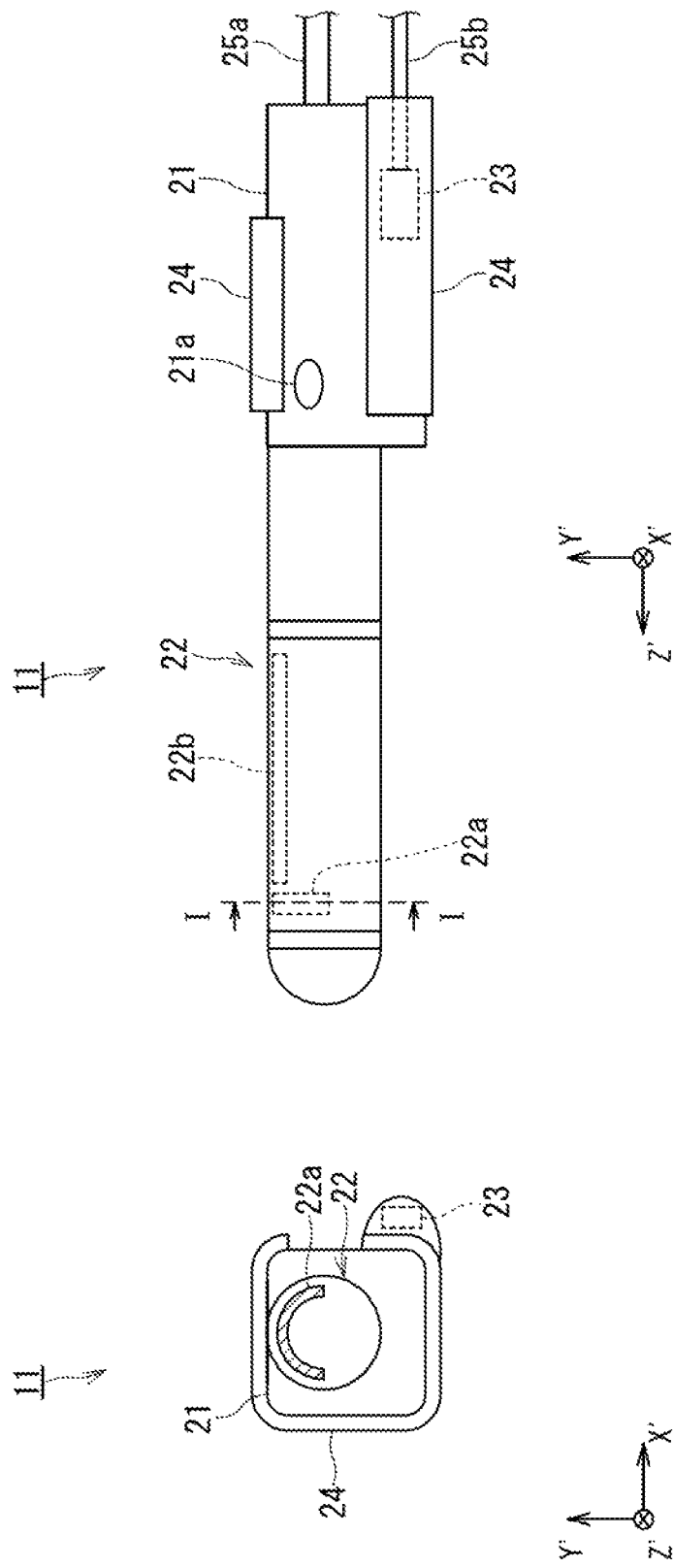
FIG. 2 is a diagram illustrating a configuration example of the ultrasonic probe.

FIG. 2 is a diagram illustrating a configuration example of the ultrasonic probe 11.

In the present embodiment, for the purpose of illustration, an X'Y'Z' coordinate system is defined with respect to a position of a sensor, assuming that a direction along an axis of a distal end part of the probe body 22 in the ultrasonic probe 11 is a Z'-axis, a direction orthogonal to the Z'-axis and going toward center positions of a first piezoelectric transducer set 22a and a second piezoelectric transducer set 22b from the Z'-axis is a Y'-axis, and a direction orthogonal to the Y'-axis and the Z'-axis is an X'-axis. A left side of FIG. 2 illustrates an I-I sectional (X'-Y' section) diagram of the ultrasonic probe 11 illustrated on a right side of FIG. 2, and the right side of FIG. 2 illustrates a diagram of the ultrasonic probe 11 when seen from a side. The ultrasonic probe 11 includes a handle portion 21, the probe body 22, a sensor 23, a sensor cover 24, and a cable 25 (25a, 25b). The handle portion 21 includes a switch 21a for instructing switching of a scan mode.

The probe body 22 includes the first piezoelectric transducer set 22a in which piezoelectric transducers are arranged on a plane orthogonal to the Z'-axis and along an arc direction around the Z'-axis and the second piezoelectric transducer set 22b in which the piezoelectric transducers are arranged so as to be in parallel with the Z'-axis. Each of piezoelectric transducers included in the piezoelectric transducer sets 22a and 22b is an electroacoustic conversion element and has a function of converting an electric pulse to an ultrasonic pulse (transmitted ultrasonic wave) in transmission and of converting an ultrasonic reflected wave (received ultrasonic wave) to an electric signal (received signal) in reception.

The first piezoelectric transducer set 22a includes a transducer row including the piezoelectric transducers arranged with an azimuth direction set in a direction along an X'-Y' plane, for example. The first piezoelectric transducer set 22a forms a convex array along a surface shape of the distal end part of the probe body 22, for example. Hereinafter, a case where the first piezoelectric transducer set 22a forms the convex array will be described as an example.

The second piezoelectric transducer set 22b includes a transducer row including the piezoelectric transducers arranged with an azimuth direction set in a direction along the Z'-direction, for example. The second piezoelectric transducer set 22b forms a linear array along the surface shape of the distal end part of the probe body 22. Hereinafter, a case where the second piezoelectric transducer set 22b is a linear array will be described as an example.

In general, when one to three piezoelectric transducer rows each including the piezoelectric transducers arranged along the azimuth direction are arranged along an elevation direction, a lens material (not shown) for converging the ultrasonic waves transmitted from the piezoelectric transducer row in the elevation direction is provided on a front surface side (acoustic emission surface side) of the transducer row or those transducer rows. On the other hand, when a sufficient number of transducer rows each including the piezoelectric transducers arranged along the azimuth direction are arranged along the elevation direction, an electronic focus is used for converging the ultrasonic waves transmitted from the transducer row in the elevation direction.

On the front surface side of each of the arrays 22a and 22b, an acoustic matching layer (not shown) for reducing mismatch of acoustic impedance with a living body can be arranged, and on a rear surface side of each of the arrays 22a and 22b, a backing material (not shown) for reducing reflection from the rear surface side can be arranged. Moreover, each of the piezoelectric transducers of the arrays 22a and 22b can be electrically connected to various circuits provided in the probe body 22 and the main body 12. The convex array 22a and the linear array 22b are connected to a transceiver circuit 36 which will be described later through a switch circuit (not shown) provided in the ultrasonic probe 11. The switch circuit is a circuit for switching (connection) between the convex array 22a and the linear array 22b.

The sensor 23 detects and outputs its own position P0 [X, Y, Z] or information corresponding to that. Moreover, the sensor 23 can detect and output its own posture [$\theta_x$, $\theta_y$, $\theta_z$] or information corresponding to that. When the sensor 23 detects positions of at least two spots or information corresponding to them, for example, a posture of the sensor 23 can be detected from a detection result of the at least two spots. The sensor 23 in the present embodiment detects a size and a direction of a magnetic field generated by a magnetic field generator 39 which will be described later and detects and outputs a position and a posture of the sensor on the basis of the detected size and direction of the magnetic field. It is preferable that the sensor 23 is used both in scan using the convex array 22a and in scan using the linear array 22b. That is because a size of the ultrasonic probe 11 is to be suppressed. The sensor 23 may be a so-called nine-axis sensor including at least any one of a three-axis gyro sensor for detecting an angular speed of three axes in a three-dimensional space, a three-axis acceleration sensor for detecting acceleration of the three axes in the three-dimensional space, and a three-axis geomagnetic sensor for detecting geomagnetism of the three axes in the three-dimensional space. The position and the posture of the sensor 23 can be also regarded as a position and a posture of the ultrasonic probe.

The sensor cover 24 can hold the sensor 23 and is detachably attached to the probe body 22 while holding the sensor 23. The sensor 23 and the sensor cover 24 may be a part of the probe body 22.

The cable 25a connects a signal line of the probe body 22 to a transmission circuit 361 and a reception circuit 362 (both are illustrated in FIG. 1) of the transceiver circuit 36 which will be described later. The cable 25b connects a signal line of the sensor 23 to processing circuitry 31 (illustrated in FIG. 1). Alternatively, the cable 25b is connected to an external device (not shown) connected to the processing circuitry 31. Processing circuitry (not shown) included in this external device detects a position of the sensor 23 on the basis of information output by the sensor 23 when the sensor 23 outputs not the position itself but information corresponding to that, for example. The processing circuit included in this external device detects a posture of the sensor 23 on the basis of information output by the sensor 23 when the sensor 23 outputs not the posture itself but information corresponding to the posture, for example. Alternatively, the processing circuit included in this external device detects a posture of the sensor 23 on the basis of detected positions of at least two spots, for example. That is, the processing circuit included in this external device detects the position or the posture on the basis of the output from the sensor 23 when the sensor 23 does not output the position itself or the posture itself. The processing included in this external device outputs the detected position or posture to the processing circuitry 31. Detection by the processing circuit included in this external device may be alternatively executed by the processing circuitry 31.

Returning to the description of FIG. 1, the main body 12 includes the processing circuitry 31, a storage portion (memory circuit, for example) 32, an input portion (input circuit, for example) 33, a display portion (display, for example) 34, a reference signal generation circuit 35, the transceiver circuit 36, an echo data processing circuit 37, an image generation circuit 38, and the magnetic field generator (magnetic transmitter) 39.

The processing circuitry 31 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like.

The processing circuitry 31 may be a single processing circuit or a combination of multiple processing circuits. In the latter case, the memory circuit 32 includes multiple memory circuit elements each storing an element of a program that the processing circuitry 31 executes, and each corresponding to the processing circuit. Alternatively, in the latter case, the memory circuit 32 includes a single memory circuit storing the program that the processing circuitry 31 executes, and corresponding to the multiple processing circuits.

The memory circuit 32 includes a semiconductor memory element such as a RAM (Random Access Memory), a flash memory and the like, a hard disk, an optical disk and the like. The memory circuit 32 may be a portable media such as an USB (Universal Serial bus) memory, a DVD (Digital Video Disk) and the like. The memory circuit 32 stores various processing programs (in addition to application programs, OS (Operating System) and the like are also included), data required for execution of the programs, and medical images used in the processing circuitry 31. The OS may include a GUI (Graphical User Interface) which enables basic operations by the input circuit 33 by using many graphics in display of information on the display 34 to an operator.

The memory circuit 32 stores first information relating to a positional relationship between a position of the sensor 23 attached on the ultrasonic probe 11 and a position of a scan plane of the convex array 22a. Moreover, the memory circuit 32 stores second information relating to a positional relationship between the position of the sensor 23 attached on the ultrasonic probe 11 and a position of the scan plane of the linear array 22b.

Figure 3:
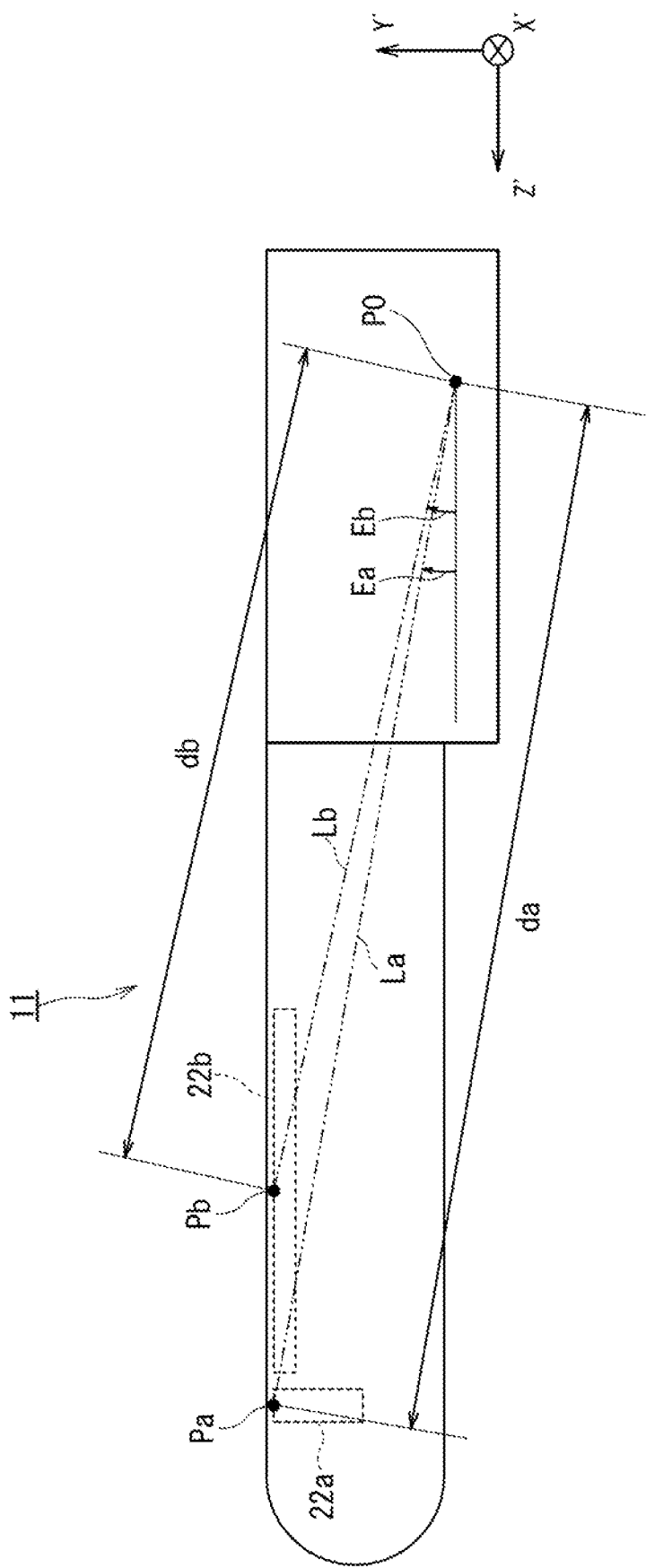
FIG. 3 is a diagram for explaining first information and second information.

FIG. 3 is a diagram for explaining the first information and the second information.

As illustrated in FIG. 3, the position of the sensor 23 attached on the ultrasonic probe 11 is defined as P0, a scan plane position of the convex array 22a as Pa, and a scan plane position of the linear array 22b as Pb. The scan plane position Pa of the convex array 22a may be the center position of the piezoelectric transducers of the convex array 22a or may be a part on the scan plane of the convex scan.

Similarly, the scan plane position Pb of the linear array 22b may be the center position of the piezoelectric transducers of the linear array 22b or may be a part on the scan plane of the linear scan. Hereinafter, a case where the scan plane position Pa of the convex array 22a is at the center position of the piezoelectric transducers of the convex array 22a and the scan plane position Pb of the linear array 22b is the center position of the piezoelectric transducers of the linear array 22b will be described.

Since the positions P0, Pa, and Pb in the X'Y'Z' coordinate system are known, a distance da between the position P0 and the position Pa is known information, and a distance db between the position P0 and the position Pb is known information. A direction of the position Pa with respect to the position P0 is known information definable by an elevation angle Ea based on a Z'-X' plane with respect to a straight line La passing through the positions P0 and Pa, and a direction of the position Pb with respect to the position P0 is known information definable by an elevation angle Eb based on a Z'-X' plane with respect to a straight line Lb passing through the positions P0 and Pb. That is, the positions Pa and Pb in an XYZ coordinate system which will be described later are uniquely determined by the position P0 and a posture of the sensor 23 in the XYZ coordinate system and the aforementioned information. The case where azimuth angles Aa and Ab based on the Z'-axis with respect to the straight lines La and Lb are not considered by the definition of the aforementioned X'Y'Z' coordinate system is described, but the azimuth angles Aa and Ab need to be considered if definition (definition of each axis) of the coordinate system is different.

The first information in the present embodiment relates to a positional relationship between the position P0 and the position Pa or in other words, a relative relationship between the position P0 and the position Pa. The second information in the present embodiment relates to a positional relationship between the position P0 and the position Pb or in other words, a relative relationship between the position P0 and the position Pb. In the explanation using FIG. 3 as an example, the first information includes information defining the X'Y'Z' coordinate system, information on the distance da between the position P0 and the position Pa, and information on the elevation angle Ea based on the Z'-X' plane with respect to the straight line La, while the second information includes the information defining the X'Y'Z' coordinate system, information on the distance db between the position P0 and the position Pb, and information on the elevation angle Eb based on the Z'-X' plane with respect to the straight lint Lb. The first information may include information relating to the posture of the first scan plane in the X'Y'Z' coordinate system, and the second information may include information relating to the posture of the second scan plane in the X'Y'Z' coordinate system. The case where the positional relationships between the position P0 and the position Pa and between the position P0 and the position Pb are determined in a polar coordinate manner is described, but these positional relationships may be determined in a rectangular coordinate manner.

The first information may include information of distances da-1, da-2, and da-3 between each of three positions Pa-1, Pa-2, and Pa-3, for example, defining the posture of the first scan plane and the position P0, information of elevation angles Ea-1, Ea-2, and Ea-3 based on the Z'-X' plane with respect to each of a straight line La-1 passing through the position Pa-1 and the position P0, a straight line La-2 passing through the position Pa-2 and the position P0, and a straight line La-3 passing through the position Pa-3 and the position P0, and information of azimuth angles Aa-1, Aa-2, and Aa-3 based on the Z'-axis with respect to each of the straight lines La-1, La-2, and La-3. The second information may include information of distances db-1, db-2, and db-3 between each of three positions Pb-1, Pb-2, and Pb-3, for example, defining the posture of the second scan plane and the position P0, information of elevation angles Eb-1, Eb-2, and Eb-3 based on the Z'-X' plane with respect to each of a straight line Lb-1 passing through the position Pb-1 and the position P0, a straight line Lb-2 passing through the position Pb-2 and the position P0, and a straight line Lb-3 passing through the position Pb-3 and the position P0, and information of azimuth angles Ab-1, Ab-2, and Ab-3 based on the Z'-axis with respect to each of the straight lines Lb-1, Lb-2, and Lb-3. Alternatively, the posture of the scan plane may be calculated as appropriate by the processing circuitry 31 in calculation of each pixel position of images generated by the image generation circuit 38.

Returning to the description of FIG. 1, the input circuit 33 is a circuit into which a signal from an input device is input. The input device includes a pointing device (a mouse, a trackball and the like) capable of operation by an operator, a keyboard, a touch pad and the like. Here, the input device itself is assumed to be included in the input circuit 33. When the input device is operated by the operator, the input circuit 33 generates an input signal according to the operation and outputs it to the processing circuitry 31. The main body 12 may include a touch panel in which the input device is constituted integrally with the display 34.

The display 34 includes a general display output device such as a liquid crystal display, an OLED (Organic Light Emitting Diode) display and the like and displays image data generated by the image generation circuit 38 in accordance with control of the processing circuitry 31.

The reference signal generation circuit 35 generates a continuous wave or a rectangular wave having a frequency substantially equal to the center frequency of an ultrasonic pulse, for example, to the transceiver circuit 36 in accordance with the control signal from the processing circuitry 31.

The transceiver circuit 36 performs transmission/reception to/from the ultrasonic probe 11 in accordance with the control signal from the processing circuitry 31. The transceiver circuit 36 includes a transmission circuit 361 for generating a driving signal for causing the ultrasonic probe 11 to emit ultrasonic waves and a reception circuit 362 performing phase-regulation and addition to the received signal from the ultrasonic probe 11.

The transmission circuit 361 includes a rate pulse generator, a transmission delay circuit, and a pulsar, not shown. The rate pulse generator generates the rate pulse determining a repetition period of the transmitted ultrasonic waves by dividing the continuous wave or the rectangular wave supplied from the reference signal generation circuit 35 and supplies this rate pulse to the transmission delay circuit. The transmission delay circuit includes independent delay circuits in the same number (N channels) as that of the piezoelectric transducers used for transmission, gives delay time for focusing the transmitted ultrasonic waves to a predetermined depth and delay time for emitting the transmitted ultrasonic waves in a predetermined direction in order to obtain a narrow beam width in transmission and supplies this rate pulse to the pulsar. The pulsar has an independent driving circuit with N channels and generates a drive pulse for driving the piezoelectric transducers incorporated in the ultrasonic probe 11 on the basis of the rate pulse.

The reception circuit 362 includes a pre-amp, an A/D (Analog to Digital) conversion circuit, a reception delay circuit, and an addition circuit, not shown. The pre-amp is includes N channels and ensures sufficient S/N by amplifying a weak signal having been converted by the piezoelectric transducers to electric received signals. The received signals of the N channel amplified by the pre-amp to a predetermined size are converted by the A/D conversion circuit to digital signals and are sent to the reception delay circuit. The reception delay circuit gives focusing delay time for focusing the ultrasonic reflected waves from the predetermined depth and deflection delay time tor setting reception directivity to a predetermined direction to each of the received signals of the N channels output from the A/D conversion circuit. An addition circuit performs phase-regulation and addition of the received signals from the reception delay circuit (addition by having phases of the received signals obtained from the predetermined direction matched).

The echo data processing circuit 37 executes processing for generating an ultrasonic image with respect to echo data input from the reception circuit 362 in accordance with the control signal from the processing circuitry 31. For example, the echo data processing circuit 37 executes B-mode processing such as logarithm compression processing, envelope detection processing and the like and Doppler processing such as orthogonal detection processing, filter processing and the like.

The image generation circuit 38 generates ultrasonic image data by scan/converting data input from the echo data processing circuit 37 by a scan converter in accordance with a control signal from the processing circuitry 31. Then, the image generation circuit 38 has the ultrasonic image based on the ultrasonic image data displayed on the display 34. The ultrasonic image data in the present embodiment includes at least any one of form image data (including B-mode image) expressing form information in the object, Doppler image data expressing distribution of blood flow information in the object, tissue characterization image data expressing tissue characteristics such as elasticity, viscosity, attenuation and the like in the object. The ultrasonic image data in the present embodiment includes at least one of two-dimensional image data and three-dimensional image data.

The magnetic field generator 39 generates a magnetic field. The XYZ coordinate system in the present embodiment may be defined on the basis of the position and the posture of the magnetic field generator 39 or may be defined without depending on the position and the posture of the magnetic field generator 39. The magnetic field generator 39 generates a magnetic field. In synchronization with that, the sensor 23 sequentially detects its own position P0 [x, y, z] in the XYZ coordinate system and its own posture [$\alpha$, $\beta$, $\gamma$] in the XYZ coordinate system.

Subsequently, functions of the ultrasonic diagnostic apparatus 1 according to the present embodiment will be described.

Figure 4:
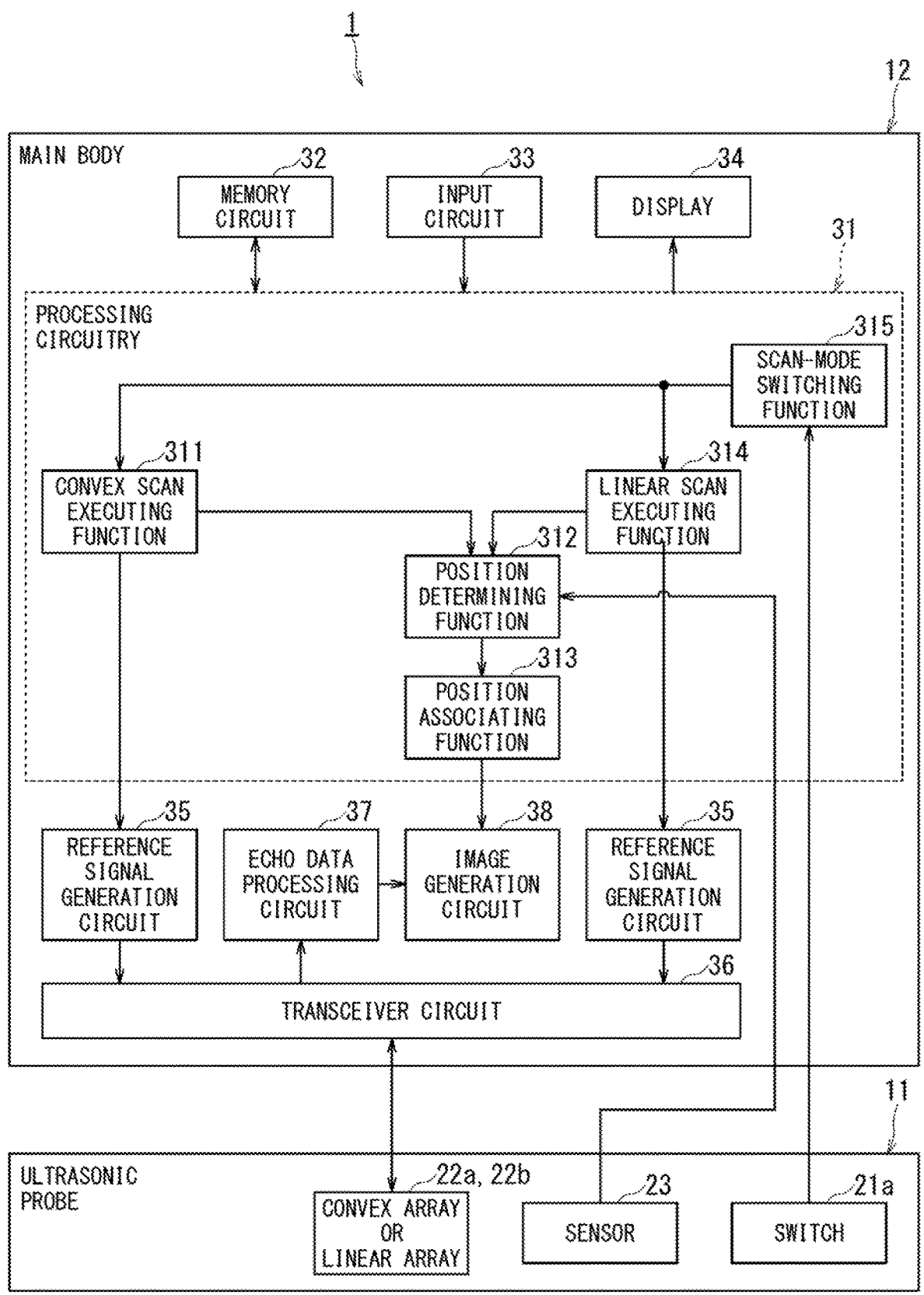
FIG. 4 is a block diagram illustrating functions of the ultrasonic diagnostic apparatus according to the present embodiment.

FIG. 4 is a block diagram illustrating the functions of the ultrasonic diagnostic apparatus 1 according to the present embodiment.

The ultrasonic diagnostic apparatus 1 functions as a convex scan executing function 311, a position determining function 312, a position associating function 313, a linear scan executing function 314, and a scan-mode switching function 315 by execution of programs by the processing circuitry 31. A case where the functions 311 to 315 function in a software manner will be described as an example, but some of or all of the functions 311 to 315 may be provided as a digital circuit in the ultrasonic diagnostic apparatus 1.

Figure 5:
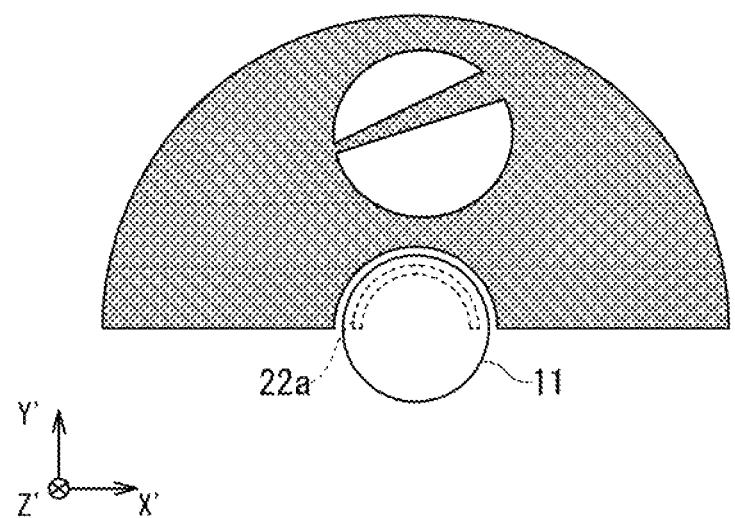
FIG. 5 is a conceptual diagram illustrating a relationship of a convex array and an image generated by a convex scan using the convex array.
Figure 6:
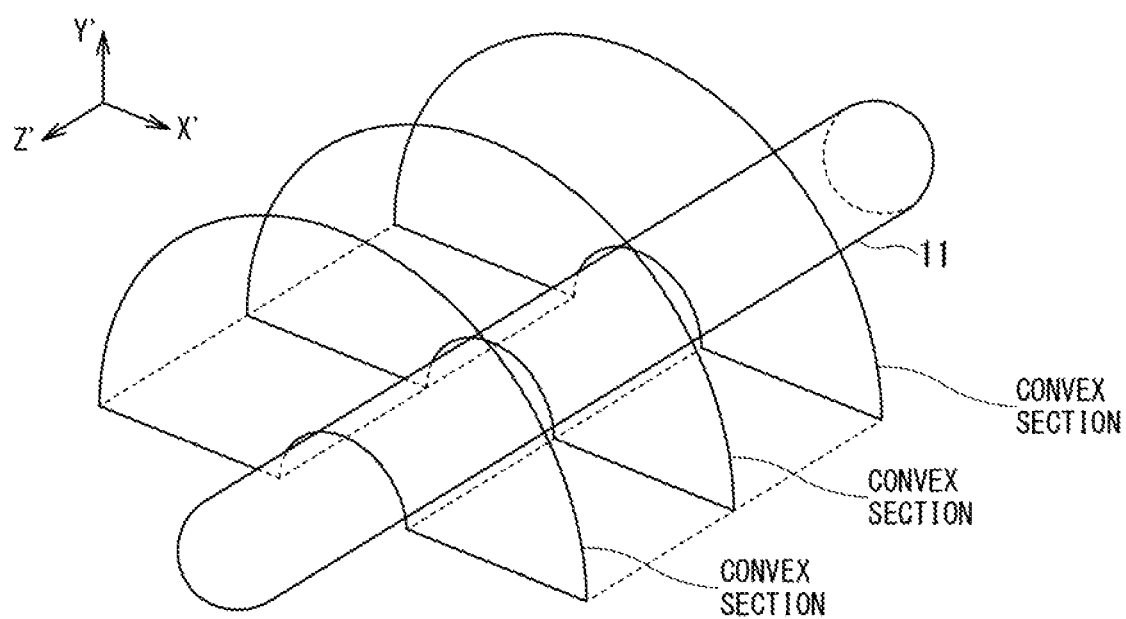
FIG. 6 is a diagram illustrating movement of a first scan plane when the ultrasonic probe is made to slide along the Z'-axis during the convex scan.

The convex scan executing function 311 is a function of executing convex scan by controlling the convex array 22a of the ultrasonic probe 11 through the reference signal generation circuit 35. The image generation circuit 38 generates images relating to frames on the basis of an output from the convex array 22a during the convex scan. The processing circuitry 31 sequentially displays (live-display) the images relating to the respective frames generated by the image generation circuit 38 on the display 34. For example, if the ultrasonic probe 11 in the present embodiment is to be used with the purpose of puncture treatment to prostate, the live-display of the images relating to the respective frames is effective in searching a portion to be punctured, for example. FIG. 5 is a conceptual diagram illustrating a relationship of the convex array 22a and an image generated by the convex scan using the convex array 22a. FIG. 6 is a diagram illustrating movement of the first scan plane when the ultrasonic probe 11 is made to slide along the Z'-axis during the convex scan, that is, convex sections formed by the moving first scan plane. The convex sections are all substantially in parallel with the X'Y' plane.

Returning to the description of FIG. 4, the position determining function 312 is a function of determining relative positions of images relating to respective frames generated by the image generation circuit 38 on the basis of the output of the sensor 23 and the first information stored in the memory circuit 32. For example, the processing circuitry 31 determines a position of an image of a first frame in the XYZ coordinate system on the basis of the position P0 and the posture of the sensor 23 in the XYZ coordinate system output by the sensor 23 at timing when data to be a base for the image of the first frame is collected and the first information read out by the processing circuitry 31 from the memory circuit 32 and determines a position of an image of a second frame in the XYZ coordinate system on the basis of the position P0 and the posture of the sensor 23 in the XYZ coordinate system output by the sensor 23 at timing when data to be a base for the image of the second frame is collected and the first information read out by the processing circuitry 31 from the memory circuit 32.

That is, the processing circuit determines a position of an image of an m-th frame in the XYZ coordinate system on the basis of the position P0 and the posture of the sensor 23 in the XYZ coordinate system output by the sensor 23 at timing when data to be a base for the image of the m-th frame is collected and the first information read out by the processing circuitry 31 from the memory circuit 32.

The processing circuitry 31 can determine a position of an image of another frame with respect to a position of an image of a k-th frame, for example (relative positions of the image of the k-th frame and the image of another frame) by the position determining function 312.

The position associating function 313 is a function of associating a relative position of an image determined by the position determining function 312 with each of the images generated by the image generation circuit 38 in the convex scan. The position associating function 313 may attach the relative position to each of the images generated in the convex scan or may generate an association table for associating the images with the respective relative positions. Instead of the relative position or in addition to the relative position, the position in the XYZ coordinate system (absolute position) may be attached. An association table associating the images with the respective absolute positions may be generated.

The image generation circuit 38 generates volume data as three-dimensional image data by aligning the images generated in the convex scan in accordance with the associated relative positions and by executing interpolation processing as necessary. The image generation circuit 38 generates a three-dimensional image on the basis of the volume data. That is, the image generation circuit 38 can generate the three-dimensional image data (first three-dimensional image data) on the basis of an output of the ultrasonic probe 11 obtained by ultrasonic transmission/reception using the convex array 22a, an output of the sensor 23, and the first information. The image generation circuit 38 displays the generated three-dimensional image. Here, the three-dimensional image means an image generated by applying three-dimensional image processing including rendering processing such as volume rendering, surface rendering, global illumination and the like and MPR (Multi-Planar Reconstruction) processing and the like to the three-dimensional image data.

Figure 7:
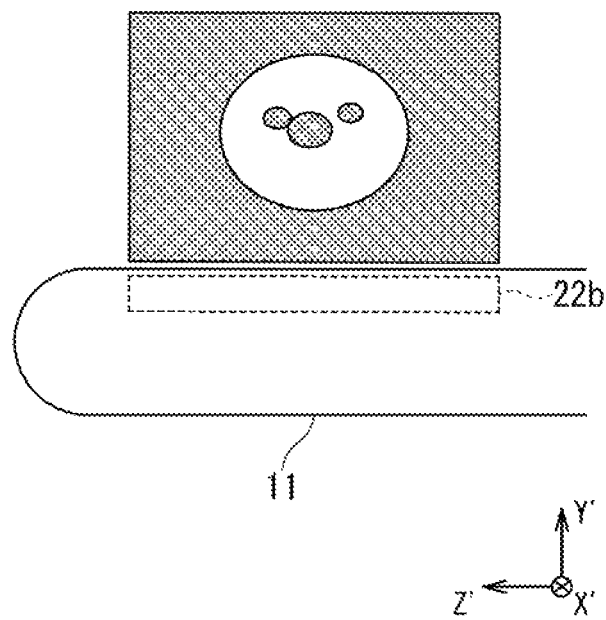
FIG. 7 is a conceptual diagram illustrating a relationship of the linear array and an image generated by a linear scan using the linear array.
Figure 8:
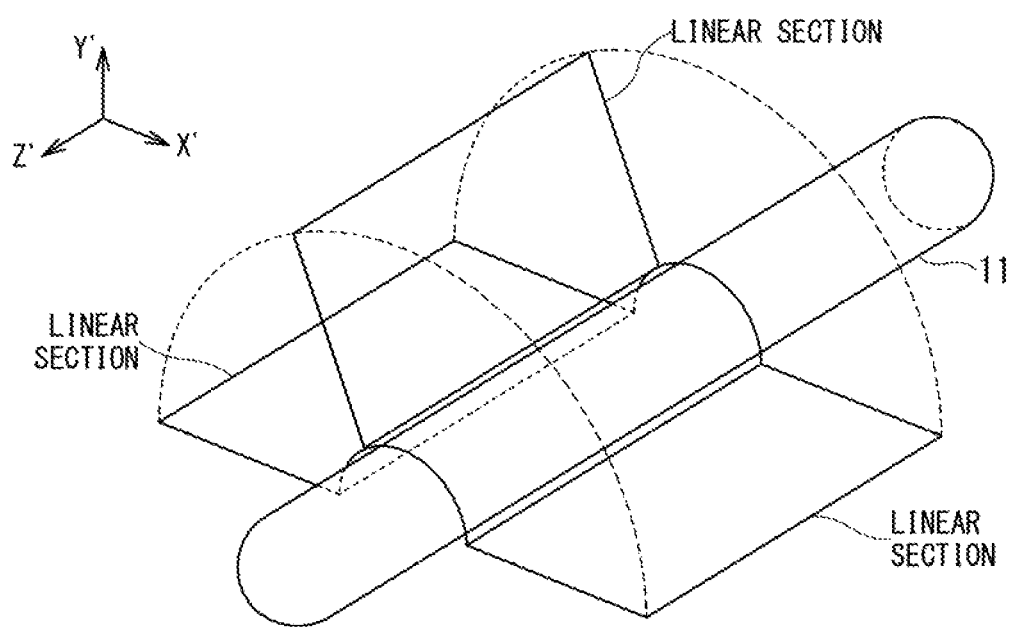
FIG. 8 is a diagram illustrating movement of a second scan plane when the ultrasonic probe is made to rotate around the Z'-axis during the linear scan.

The linear scan executing function 314 is a function of executing linear scan by controlling the linear array 22b of the ultrasonic probe 11 through the reference signal generation circuit 35. The image generation circuit 38 generates images relating to respective frames on the basis of an output from the linear array 22b during the linear scan. The processing circuitry 31 sequentially live-displays the images relating to the respective frames generated by the image generation circuit 38 on the display 34. For example, if the ultrasonic probe 11 in the present embodiment is to be used with the purpose of puncture treatment for prostate, the live-display of the images relating to the respective frames is effective in searching a position of a puncture needle, for example. FIG. 7 is a conceptual diagram illustrating a relationship of the linear array 22b and an image generated by the linear scan using the linear array 22b. FIG. 8 is a diagram illustrating movement of the second scan plane when the ultrasonic probe 11 is made to rotate around the Z'-axis during the linear scan, that is, linear sections formed by the moving second scan plane. The linear sections have different rotation angles in a rotating direction around the Z'-axis.

Returning to the description of FIG. 4, the position determining function 312 is a function of determining relative positions of the images relating to the respective frames generated by the image generation circuit 38 on the basis of the output of the sensor 23 and the second information stored in the memory circuit 32. For example, the processing circuitry 31 determines a position of an image of a first frame in the XYZ coordinate system on the basis of the position P0 and the posture of the sensor 23 in the XYZ coordinate system output by the sensor 23 at timing when data to be a base for the image of the first frame is collected and the second information read out by the processing circuitry 31 from the memory circuit 32 and determines a position of an image of a second frame in the XYZ coordinate system on the basis of the position P0 and the posture of the sensor 23 in the XYZ coordinate system output by the sensor 23 at timing when data to be a base for the image of the second frame is collected and the second information read out by the processing circuitry 31 from the memory circuit 32.

The position associating function 313 is a function of associating a relative position of an image determined by the position determining function 312 with each of images generated by the image generation circuit 38 in the linear scan. The position associating function 313 may attach the relative position to each of the images generated in the linear scan or may generate an association table for associating the images with the respective relative positions. Instead of the relative position or in addition to the relative position, the position in the XYZ coordinate system (absolute position) may be attached. An association table associating the images with the respective absolute positions may be generated.

The image generation circuit 38 generates volume data as three-dimensional image data by aligning the images generated in the linear scan in accordance with the associated relative positions and by executing interpolation processing as necessary. Moreover, the image generation circuit 38 generates a three-dimensional image on the basis of the volume data. That is, the image generation circuit 38 can generate three-dimensional image data (second three-dimensional image data) on the basis of an output of the ultrasonic probe 11 obtained by the ultrasonic transmission/reception using the linear array 22b, an output of the sensor 23, and the second information. The image generation circuit 38 displays the generated three-dimensional image.

Figure 9:
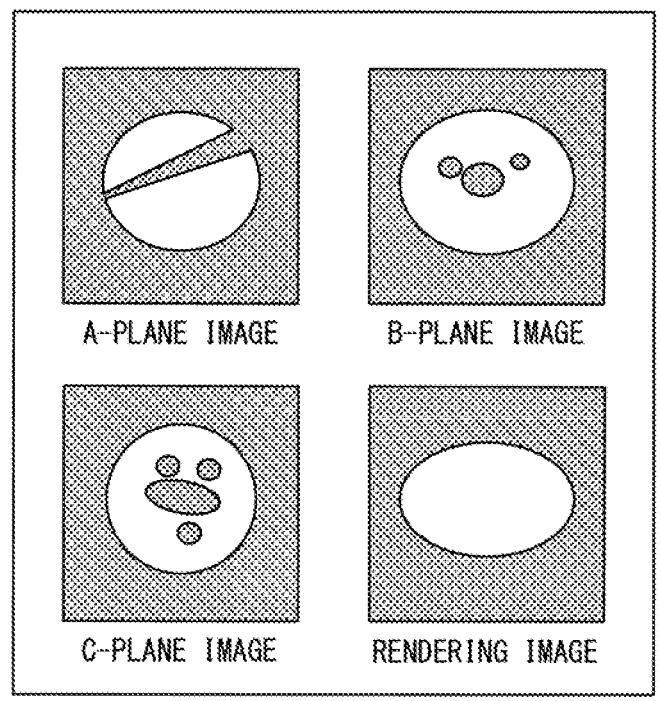
FIG. 9 is a diagram illustrating a first display example of a three-dimensional image.

FIG. 9 is a diagram illustrating a first display example of the three-dimensional image.

FIG. 9 illustrates the first display example of the three-dimensional image based on the volume data generated from the sectional images generated in a B mode. As illustrated in FIG. 9, the three-dimensional images can be displayed in parallel. In FIG. 9, as the three-dimensional images, orthogonal 3-sectional images (A-plane image, B-plane image, and C-plane image) and a rendering image are illustrated. The sectional images obtained by the convex scan and those obtained by the linear scan are both equal. The sectional images are not limited to those generated in the B mode but may be those generated in a color Doppler mode or in an elasto mode.

Figure 10:
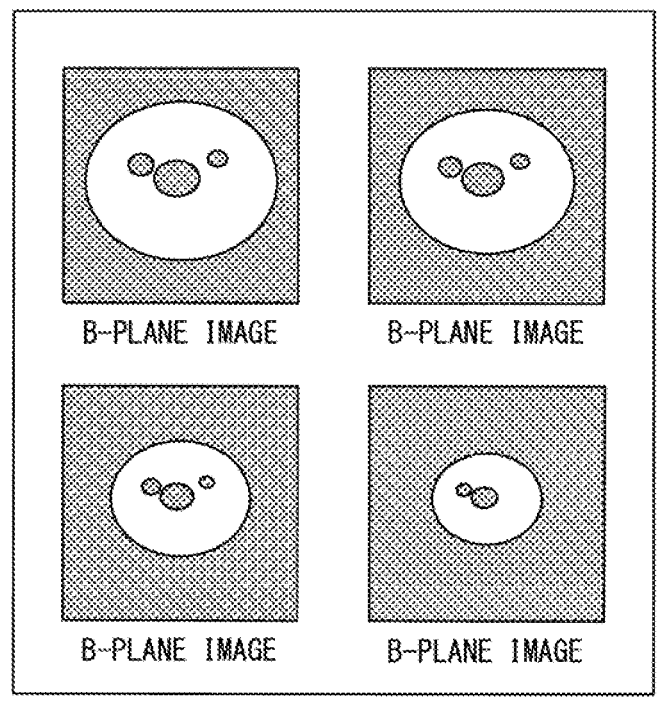
FIG. 10 is a diagram illustrating a second display example of a three-dimensional image.

FIG. 10 is a diagram illustrating a second display example of the three-dimensional image.

FIG. 10 illustrates the second display example of the three-dimensional image based on the volume data generated from the sectional images generated in the B mode. As illustrated in FIG. 10, the three-dimensional images can be displayed in parallel. In FIG. 10, as the three-dimensional images, four B-plane images in parallel are illustrated. The sectional images obtained by the convex scan and those obtained by the linear scan are both equal. Moreover, the sectional images are not limited to those generated in the B mode but may be generated in the color Doppler mode or in the elasto mode.

Returning to the description of FIG. 4, the scan-mode switching function 315 includes a function of switching the scan mode from the convex scan to the linear scan if the switch 21a of the ultrasonic probe 11 is pressed during execution of the convex scan by the convex scan executing function 311. Moreover, the scan-mode switching function 315 includes a function of switching the scan mode from the linear scan to the convex scan if the switch 21a of the ultrasonic probe 11 is pressed during execution of the linear scan by the linear scan executing function 314. The switching of the scan mode is not an indispensable function for the ultrasonic diagnostic apparatus 1.

Subsequently, operations of the ultrasonic diagnostic apparatus 1 according to the present embodiment will be described by using FIGS. 4, 11, and 12.

Figure 11:
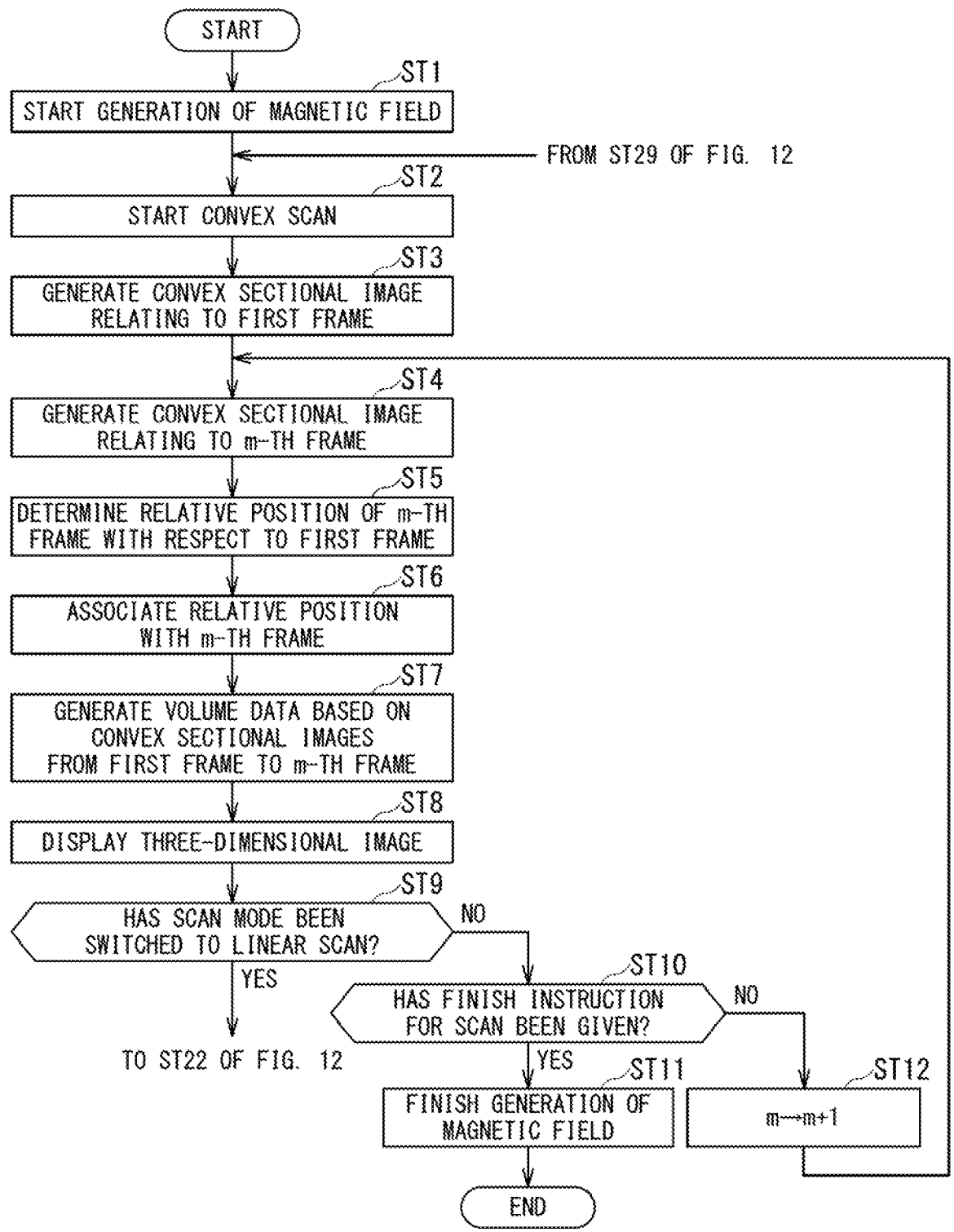
FIG. 11 is one part of a flowchart illustrating operations of the ultrasonic diagnostic apparatus according to the present embodiment.
Figure 12:
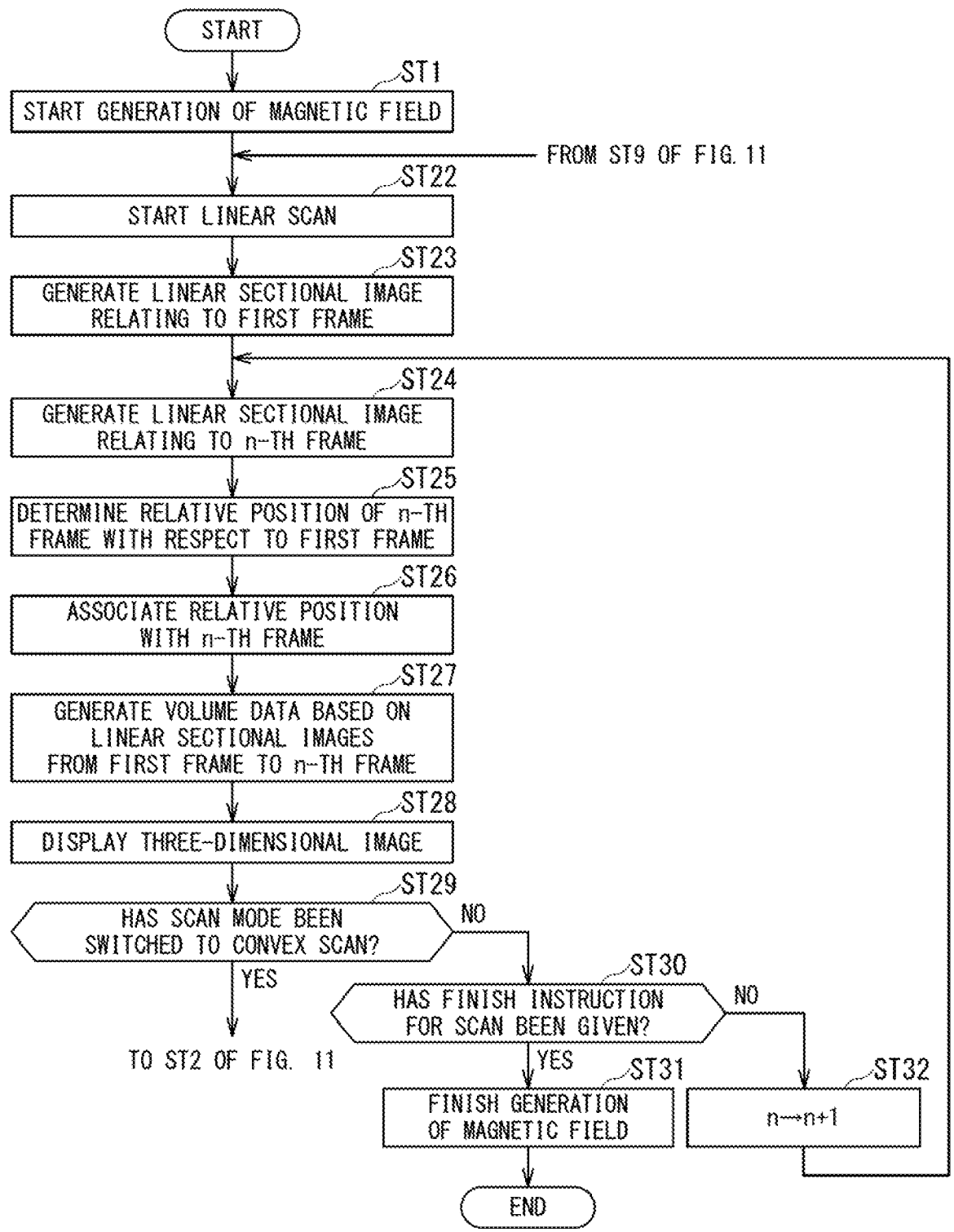
FIG. 12 is the other part of the flowchart illustrating the operations of the ultrasonic diagnostic apparatus according to the present embodiment.

FIGS. 11 and 12 are flowcharts illustrating the operations of the ultrasonic diagnostic apparatus 1 according to the present embodiment.

In FIGS. 4 and 11, the convex scan executing function 311 of the ultrasonic diagnostic apparatus 1 controls the magnetic field generator 39 (illustrated in FIG. 1) and starts generation of a magnetic field in a three-dimensional direction (Step ST1). The convex scan executing function 311 starts the convex scan by controlling the convex array 22a of the ultrasonic probe 11 when start of scan is input through the input circuit 33 (Step ST2).

The image generation circuit 38 generates a convex sectional image relating to the first frame during the convex scan (Step ST3). The image generation circuit 38 generates a convex sectional image relating to an m-th frame during the convex scan (Step ST4). The image generation circuit 38 may display the convex sectional image relating to the m-th frame on the display 34. In that case, the image generation circuit 38 can also live-display the convex sectional image by updating display of the convex sectional image relating to a frame prior to the m-th frame to the convex sectional image relating to the m-th frame.

The position determining function 312 determines a relative position of the convex sectional image relating to the m-th frame with respect to the convex sectional image relating to the first frame generated by the image generation circuit 38 on the basic of an output of the sensor 23 relating to the m-th frame and the first information stored in the memory circuit 32 (Step ST5).

The position associating function 313 associates the relative position of the scan plane determined at Step ST5 with a convex sectional image relating to the m-th frame generated by the convex scan by the image generation circuit 38 (Step ST6). The image generation circuit 38 generates the volume data as the three-dimensional image data on the basis of convex sectional images from the first frame to the m-th frame with which the relative position is associated during the convex scan (Step ST7). After a m−1-th volume data is generated on the basis of the convex sectional images from the first frame to the m−1-th frame, when the m-th volume data is to be generated on the basis of the convex sectional images from the first frame to the m-th frame, the m-th volume data is newly generated separately from the m−1-th volume data at Step ST7. That is, m pieces of the volume data are generated. However, the case is not limiting. The m-th volume data may be generated by updating the m−1-th volume data by the m-th convex sectional image, for example. That is, one piece of volume data is generated.

The image generation circuit 38 generates a three-dimensional image on the basis of the volume data generated at Step ST7 and displays the three-dimensional image on the display 34 (Step ST8). That is, at Step ST8, three-dimensional images based on the volume data of the respective frames is live-displayed. Consider a case where, after the m−1-th volume data is generated on the basis of the convex sectional images from the first frame to the m−1-th frame, the m-th volume data is generated on the basis of the convex sectional images from the first frame to the m-th frame. In that case, since data ranges are different between the m−1-th volume data and the m-th volume data, a display range of the three-dimensional image fluctuates during live-display, for example. Moreover, the image generation circuit 38 has the volume data generated by the Step ST7 and the three-dimensional image generated at Step ST8 stored in the memory circuit 32.

The scan-mode switching function 315 determines whether or not the scan mode has been switched to the linear scan in accordance with whether or not the switch 21a of the ultrasonic probe 11 has been pressed during the convex scan (Step ST9). If the determination at Step ST9 is YES, that is, if it is determined that the scan mode has been switched to the linear scan, the scan-mode switching function 315 finishes the convex scan and the routine proceeds to Step ST22 illustrated in FIG. 12.

On the other hand, if the determination at Step ST9 is NO, that is, if it is determined that the scan mode has not been switched to the linear scan, the scan-mode switching function 315 determines whether or not the scan should be finished in accordance with whether or not a finish instruction has been given by the operator during the convex scan (Step ST10). If the determination at Step ST10 is YES, that is, if it is determined that the scan is to be finished, the convex scan executing function 311 finishes generation of the magnetic field in the three-dimensional direction by controlling the magnetic field generator 39 (Step ST11), whereby the scan is finished.

If the determination at Step ST10 is NO, that is, it is determined that the scan is not to be finished, the image generation circuit 38 proceeds by one frame (Step ST12) and generates a convex sectional image relating to the m+1-th frame (Step ST4).

In FIGS. 4 and 12, the linear scan executing function 314 of the ultrasonic diagnostic apparatus 1 starts the linear scan by controlling the linear array 22b of the ultrasonic probe 11 when a start of scan is input through the input circuit 33 (Step ST22).

The image generation circuit 38 generates a linear sectional image relating to the first frame during the linear scan (Step ST23). The image generation circuit 38 generates a linear sectional image relating to an n-th frame during the linear scan (Step ST24). Reference character n is an integer of 2 or more. The image generation circuit 38 may display the linear sectional image relating to the n-th frame on the display 34. In that case, the image generation circuit 38 can live-display the linear sectional image by updating display of the linear sectional image relating to a frame prior to the n-th frame by the linear sectional image relating to the n-th frame.

The position determining function 312 determines a relative position of the linear sectional image relating to the n-th frame with respect to the linear sectional image relating to the first frame generated by the image generation circuit 38 on the basis of an output of the sensor 23 relating to the n-th frame and the second information stored in the memory circuit 32 (Step ST25).

The position associating function 313 associates a relative position of the scan plane determined at Step ST25 with the linear sectional image relating to the n-th frame generated in the linear scan by the image generation circuit 38 (Step ST26). The image generation circuit 38 generates the volume data as the three-dimensional image data on the basis of linear sectional images from the first frame to the n-th frame with which the relative position is associated during the linear scan (Step ST27). After an n−1-th volume data is generated on the basis of the linear sectional images from the first frame to the n−1-th frame, when the n-th volume data is to be generated on the basis of the linear sectional images from the first frame to the n-th frame, n-th volume data is newly generated separately from the n−1-th volume data at Step ST27. That is, n pieces of the volume data are generated. However, that case is not limiting. The n-th volume data may be generated by updating the n−1-th volume data by the n-th linear sectional image, for example. That is, one piece of volume data is generated.

The image generation circuit 38 generates a three-dimensional image on the basis of the volume data generated at Step ST27 and displays the three-dimensional image on the display 34 (Step ST28). That is, at Step ST28, three-dimensional images based on the volume data of the respective frames is live-displayed. Consider a case where, after the n−1-th volume data is generated on the basis of the linear sectional images from the first frame to the n−1-th frame, the n-th volume data is generated on the basis of the linear sectional images from the first frame to the n-th frame. In that case, since data ranges are different between the n−1-th volume data and the n-th volume data, a display range of the three-dimensional image fluctuates during live-display, for example. Moreover, the image generation circuit 38 has the volume data generated at the Step ST27 and the three-dimensional image generated at Step ST28 stored in the memory circuit 32.

The scan-mode switching function 315 determines whether or not the scan mode has been switched to the convex scan in accordance with whether or not the switch 21a of the ultrasonic probe 11 has been pressed during the linear scan (Step ST29). If the determination at Step ST29 is YES, that is, if it is determined that the scan mode has been switched to the convex scan, the scan-mode switching function 315 finishes the linear scan and the routine proceeds to Step ST2 illustrated in FIG. 11.

On the other hand, if the determination at Step ST29 is NO, that is, if it is determined that the scan mode has not been switched to the convex scan, the scan-mode switching function 315 determines whether or not the scan should be finished in accordance with whether or not a finish instruction has been given by the operator during the linear scan (Step ST30). If the determination at Step ST30 is YES, that is, if it is determined that the scan is to be finished, the linear scan executing function 314 finishes generation of the magnetic field by controlling the magnetic field generator 39 (Step ST31), whereby the scan is finished.

If the determination at Step ST30 is NO, that is, if it is determined that the scan is not to be finished, the image generation circuit 38 proceeds by one frame (Step ST32) and generates a linear sectional image relating to the n+1-th frame (Step ST24).

In FIGS. 11 and 12, the operation of executing the linear scan after the convex scan is executed first is described, but the operation may be such that the convex scan is executed after the linear scan is executed first. Alternatively, it may be so configured that, after the convex scan is started at Step ST2 illustrated in FIG. 11, the live-display using the convex sectional images is performed, and the operation at Step ST3 and after is started for the first frame after switching is performed separately. This also applies to the linear scan.

(First Variation)

In the aforementioned embodiment, the case where the second information includes information relating to the positional relationship between the position P0 of the sensor and the second scan plane Pb is described, but when the second information includes the information relating to the positional relationship between the position Pa of the first scan plane and the position Pb of the second scan plane, even if the second information does not include the information relating to the positional relationship between the position P0 of the sensor and the second scan plane Pb, the second three-dimensional image data can be generated. In this case, the image generation circuit 38 generates the second three-dimensional image data on the basis of the output of the ultrasonic probe 11 obtained by the ultrasonic transmission/reception using the linear array 22b, the output of the sensor 23, the first information and the second information.

(Second Variation)

Consider a case where a scan range of the ultrasonic transmission/reception using the first piezoelectric transducer set 22a illustrated in FIG. 6 (convex scan) and a scan range of the ultrasonic transmission/reception using the second piezoelectric transducer set 22b illustrated in FIG. 8

(linear scan) are overlapped. In that case, the image generation circuit 38 (illustrated in FIG. 4) can generate a sectional image corresponding to an arbitrary section for which a display request is received, as an MPR image by generating any one of the first three-dimensional image data based on the convex scan and the second three-dimensional image data based on the linear scan and by applying the three-dimensional image processing to that. However, a method for generating a display-requested sectional image is not limited to that case.

For example, the image generation circuit 38 can generate a display-requested sectional image by using at least a part of the convex sectional images from the first frame to the m-th frame (ST7 in FIG. 11), and at least a part of the linear sectional images from the first frame to the n-th frame (ST27 in FIG. 12), that is, by selectively using the both sectional images before interpolation.

In that case, the image generation circuit 38 acquires a brightness value of each pixel of the display-requested sectional image from each pixel in accordance with a distance to each pixel of the convex sectional images and each pixel of the linear sectional images. Each pixel of the display-requested sectional image, each pixel of the convex sectional images and each pixel of the linear sectional images has respective positional information. Thus, the image generation circuit 38 can employ a brightness value of a pixel of the convex and linear sectional images, the pixel being the closest to each pixel of the display-requested sectional image, as the brightness value of the each pixel of the display-requested sectional image, or can employ a brightness value calculated from brightness values corresponding to respective pixels of the convex and linear sectional images, the pixels being closer to each pixel of the display-requested sectional image, as the brightness value of the each pixel of the display-requested sectional image. The latter is a simple average value calculated from the brightness values or a weighted average value according to the distance.

As described above, when the scan range of the convex scan and the scan range of the linear scan are overlapped, a display image can be generated by selectively using information of either one of the convex sectional images and the linear sectional images by the unit of a pixel of the display-requested sectional image. As a result, deterioration of the display image can be suppressed.

(Third Variation)

The image generation circuit 38 can also generate the sectional image corresponding to an arbitrary section for which display request is accepted, as the MPR image on the basis of volume data appropriately selected, in accordance with the arbitrary section, from volume data based on the convex sectional images (hereinafter referred to as "convex volume data") and from volume data based on the linear sectional images. For example, the image generation circuit 38 generates, when a display request for the sectional image corresponding to a section in approximate parallel with the convex sections (illustrated in FIG. 6) is accepted, the display-requested sectional image on the basis of the convex volume data. Alternatively, the image generation circuit 38 generates, when a display request for the sectional image corresponding to a section in approximate parallel with any of the linear sections (illustrated in FIG. 8) is accepted, the display-requested sectional image on the basis of the linear volume data.

Figure 13A:
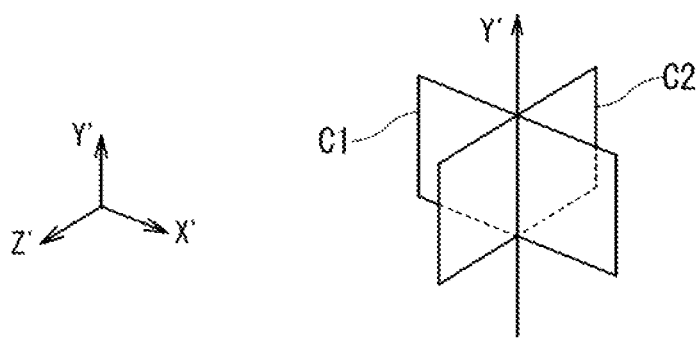
FIGS. 13A to 13C are diagrams for explaining a generation example of a sectional image corresponding to a section for which a display request is accepted.
Figure 13B:
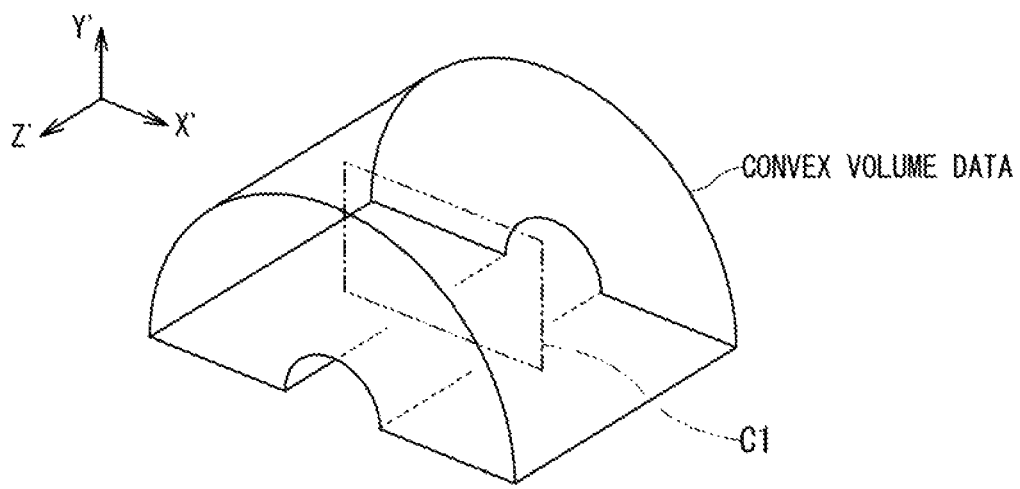
Figure 13C:
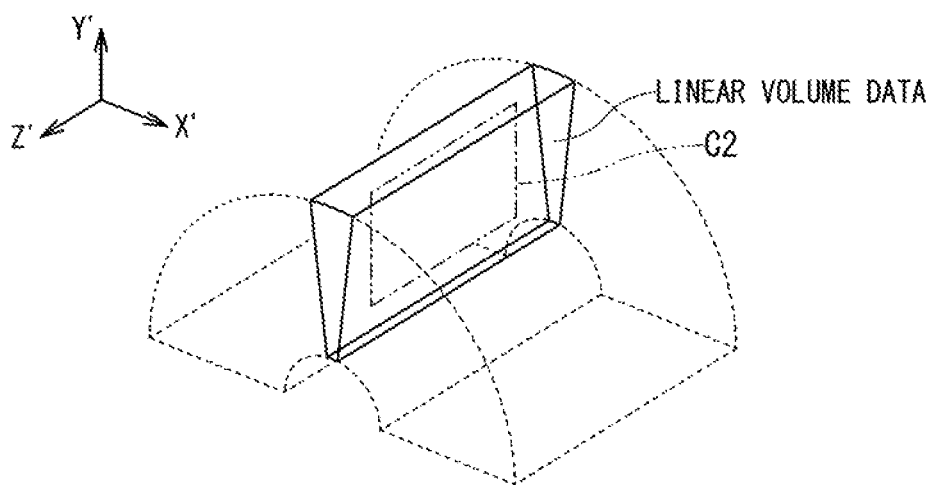

FIGS. 13A to 13C are diagrams for explaining a generation example of a sectional image corresponding to a section for which a display request is accepted.

FIG. 13A illustrates an X'Y' section C1 and a Y'Z' section C2 when sections for which a display request is accepted are orthogonal 3 sections. The X'Y' section C1 illustrated in FIG. 13A is approximate parallel with the convex sections illustrated in FIG. 6. Thus, the image generation circuit 38 can generate the sectional image corresponding to the X'Y' section C1 from the convex volume data, as illustrated in FIG. 13B. That is, the image generation circuit 38 can generate the display-requested sectional image corresponding to the X'Y' section C1 from the convex volume data based on the convex sectional images approximate parallel with the X'Y' section C1. Accordingly, it is possible to reduce the deterioration of the displayed image by the interpolation processing.

The Y'Z' section C2 illustrated in FIG. 13A is approximate parallel with any one of the linear sections illustrated in FIG. 8. Thus, the image generation circuit 38 can generate the sectional image corresponding to the Y'Z' section C2 from the linear volume data, as illustrated in FIG. 13C. That is, the image generation circuit 38 can generate the display-requested sectional image corresponding to the Y'Z' section C2 from the linear volume data based on the linear sectional images approximate parallel with the Y'Z' section C2. Accordingly, it is possible to reduce the deterioration of the displayed image by the interpolation processing.

The image generation circuit 38 only needs to have the sectional image corresponding to the remaining Z'X' section in the orthogonal 3 sections to be a sectional image based on the convex volume data or the linear volume data such as an MPR image, for example.

The case where the sections for which the display request is accepted are the orthogonal 3 sections is described by using FIGS. 13A to 13C. However, that case is not limiting. For example, as illustrated in FIG. 8, the linear sections have different rotation angles in a rotating direction around the Z'-axis. Thus, the image generation circuit 38 can generate, when a display request for the sectional image corresponding to a section with an approximate same rotating angle with the linear section, the sectional image from linear volume data relating to the linear sections with the approximate same rotating angle with the display-requested sectional image. That is, the image generation circuit 38 can generate the display-requested sectional image from the linear volume data relating to the linear sections with the approximate same rotating angle with the display-requested sectional image. Accordingly, it is possible to reduce the deterioration of the displayed image by the interpolation processing.

As described above, when the scan range of the convex scan and the scan range of the linear scan are overlapped, the display-requested sectional image can be generated, in accordance with the section of the display-required sectional image, by using appropriate one of the convex volume data and the linear volume data. As a result, deterioration of the display image can be suppressed.

According to at least one of the embodiments of the ultrasonic diagnostic apparatus and the method for generating an ultrasonic image described above, when a three-dimensional image is to be generated on each scan plane of a multi-plane probe, a three-dimensional image matching actuality can be provided.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an intracavitary ultrasonic probe including first piezoelectric transducers performing ultrasonic transmission/reception along a first scan plane, and including second piezoelectric transducers performing ultrasonic transmission/reception along a second scan plane different from the first scan plane, the first piezoelectric transducers being different from the second piezoelectric transducers;
a memory circuit configured to store first information relating to a positional relationship between a position of a sensor attached on the intracavitary ultrasonic probe and a position of the first scan plane, and to store second information relating to a positional relationship between a position of the sensor and a position of the second scan plane; and
a generation circuit configured to generate first three-dimensional image data based on an output of the intracavitary ultrasonic probe obtained by the ultrasonic transmission/reception using the first piezoelectric transducers, an output of the sensor and the first information and to generate second three-dimensional image data based on an output of the intracavitary ultrasonic probe obtained by the ultrasonic transmission/reception using the second piezoelectric transducers, an output of the sensor, and the second information, wherein
the generation circuit is configured to, when a scan range of the first three-dimensional image data and a scan range of the second three-dimensional image data are overlapped,
generate, when a display request for a sectional image corresponding to a section in parallel with the first scan plane is accepted, the display-requested sectional image based on the first three-dimensional image data among the first three-dimensional image data and the second three-dimensional image data,
generate, when a display request for a sectional image corresponding to a section in parallel with the second scan plane is accepted, the display-requested sectional image based on the second three-dimensional image data among the first three-dimensional image data and the second three-dimensional image data, and
generate, when a display request for a sectional image corresponding to a section which is not parallel to either the first scan plane or the second scan plane is accepted, the display-requested sectional image based on one of the first three-dimensional image data and the second three-dimensional image data.

2. The ultrasonic diagnostic apparatus according to claim 1, wherein
the first scan plane and the second scan plane are in a crossing relationship.

3. The ultrasonic diagnostic apparatus according to claim 2, wherein
the first piezoelectric transducers are arranged on a plane orthogonal to an axis of a probe body of the intracavitary ultrasonic probe and along an arc direction around the axis; and
the second piezoelectric transducers are arranged in parallel with the axis.

4. The ultrasonic diagnostic apparatus according to claim 1, wherein the generation circuit is configured to:
generate a first sectional image based on first echo signals or a second sectional image based on second echo signals; and
generate the first three-dimensional image data by synthesizing the first sectional image using timings based on the first position, or the second three-dimensional image data by synthesizing the second sectional image using timings based on the second position.

5. The ultrasonic diagnostic apparatus according to claim 1, wherein
the sensor is used both in scan using the first piezoelectric transducers and in scan using the second piezoelectric transducers.

6. The ultrasonic diagnostic apparatus according to claim 1, wherein the generation circuit is configured to:
generate first sectional images of first scan plane based on first echo signals and the first position, thereby generate the first three-dimensional image data based on the first sectional images;
generate second sectional images of second scan plane based on second echo signals and the second position, thereby generate the second three-dimensional image data based on the second sectional images; and
generate a sectional image corresponding to a display-requested section based on at least a part of the first sectional images and at least a part of the second sectional images.

7. The ultrasonic diagnostic apparatus according to claim 6, wherein
the generation circuit is configured to acquire a brightness value of each pixel of the sectional image corresponding to the display-requested section from the each pixel in accordance with a distance to each pixel of the first and second sectional images.

8. The ultrasonic diagnostic apparatus according to claim 1, wherein
the generation circuit is configured to generate, when a display request for a sectional image corresponding to a section in parallel with the second scan plane is accepted, the display-requested sectional image based on the second three-dimensional image data.

9. A method for generating an ultrasonic image using an ultrasonic diagnostic apparatus including (A) an intracavitary ultrasonic probe including first piezoelectric transducers performing ultrasonic transmission/reception along a first scan plane, and including second piezoelectric transducers performing ultrasonic transmission/reception along a second scan plane different from the first scan plane, (B) a memory circuit configured to store first information relating to a positional relationship between a position of a sensor attached on the intracavitary ultrasonic probe, and to store a position of the first scan plane and second information relating to a positional relationship between a position of the sensor and a position of the second scan plane, the method comprising:
generating first three-dimensional image data based on an output of the intracavitary ultrasonic probe obtained by the ultrasonic transmission/reception using the first piezoelectric transducers, an output of the sensor, and the first information;
generating second three-dimensional image data based on an output of the intracavitary ultrasonic probe obtained by the ultrasonic transmission/reception using the second piezoelectric transducers, an output of the sensor, and the second information; and generating display-requested sectional image, when a scan range of the first three-dimensional image data and a scan range of the second three-dimensional image data are overlapped, the display-requested sectional image being based on the first three-dimensional image data among the first three-dimensional image data and the second three-dimensional image data when a display request for a sectional image corresponding to a section in parallel with the first scan plane is accepted, the display-requested sectional image being based on the second three-dimensional image data among the first three-dimensional image data and the second three-dimensional image data when a display request for a sectional image corresponding to a section in parallel with the second scan plane is accepted, and the display-requested sectional image being based on one of the first three-dimensional image data and the second three-dimensional image data when a display request for a sectional image corresponding to a section which is not parallel to either the first scan plane or the second scan plane is accepted.

* * * * *